(12) United States Patent
Kroll

(10) Patent No.: US 7,640,065 B1
(45) Date of Patent: Dec. 29, 2009

(54) CARDIAC CONSTRAINT/THERAPEUTIC STIMULATION DEVICE

(75) Inventor: Mark W. Kroll, Orono, MN (US)

(73) Assignee: Pacesetter, Inc., Sylmar, GA (US)

( * ) Notice: Subject to any disclaimer, the term of this patent is extended or adjusted under 35 U.S.C. 154(b) by 643 days.

(21) Appl. No.: 11/378,491

(22) Filed: Mar. 17, 2006

(51) Int. Cl.
A61N 1/362 (2006.01)

(52) U.S. Cl. .................. 607/129; 607/119; 607/148

(58) Field of Classification Search .............. None
See application file for complete search history.

(56) References Cited

U.S. PATENT DOCUMENTS

| | | | | |
|---|---|---|---|---|
| 4,548,203 | A | 10/1985 | Tacker, Jr. et al. | 128/419 D |
| 4,821,723 | A * | 4/1989 | Baker et al. | 607/7 |
| 5,540,721 | A | 7/1996 | Kroll | 607/5 |
| 5,634,938 | A | 6/1997 | Swanson et al. | 607/5 |
| 6,076,013 | A | 6/2000 | Brennan et al. | 607/2 |
| 6,169,922 | B1 | 1/2001 | Alferness et al. | 607/5 |
| 6,370,429 | B1 | 4/2002 | Alferness et al. | 607/5 |
| 6,567,699 | B2 | 5/2003 | Alferness et al. | 607/5 |
| 6,633,780 | B1 * | 10/2003 | Berger | 607/129 |
| 2004/0010180 | A1 | 1/2004 | Scorvo | 600/16 |
| 2005/0065568 | A1 | 3/2005 | Liu et al. | 607/17 |
| 2005/0085688 | A1 | 4/2005 | Girard et al. | 600/37 |

FOREIGN PATENT DOCUMENTS

WO WO 00/28918 5/2000

OTHER PUBLICATIONS

Mark W. Kroll, "A Minimal Model of the Monophasic Defibrillation Pulse", *PACE*, Apr. 1993, Pt. 1; vol. 16, pp. 769-777.

* cited by examiner

*Primary Examiner*—Carl H. Layno
*Assistant Examiner*—Jon-Eric C. Morales

(57) ABSTRACT

A system or appliance to treat heart failure (HF) conditions. The appliance includes a structural support or cardiac constraint to limit further distension of weakened heart tissue. The appliance also includes an implantable stimulation pulse generator and controller such that the appliance can automatically monitor cardiac activity and provide therapeutic stimulations for detected arrhythmias. The appliance can also include one or more surface electrodes. The surface electrodes can be arranged on opposite sides of the heart to apply relatively spatially uniform stimulation potentials across the heart with reduced shunting around the target tissue. A surface electrode can also be arranged to wrap substantially about a periphery of the patient's heart and used with an internal electrode to apply a relatively homogeneous shock while facilitating lower voltage and smaller shocking capacitors.

7 Claims, 12 Drawing Sheets

CARDIAC CONSTRAINT/THERAPEUTIC STIMULATION DEVICE

FIELD OF THE INVENTION

The invention relates to the field of implantable cardiac devices and more particularly, to an implantable device combining both mechanical structural support to resist further distension of a diseased heart and electrical stimulation to treat arrhythmic conditions.

BACKGROUND OF THE INVENTION

Heart failure (HF) is a chronic disease afflicting millions of Americans and others around the world. HF refers generally to a disease condition characterized by a reduced capacity of the heart to effectively pump blood. HF is generally a progressive condition for which there is currently no known cure. The only currently known way to eliminate heart failure is with a heart transplant, however, the number of patients which may benefit from a heart transplant procedure far outnumber the quantity of available hearts for transplant. A variety of pharmacological therapies are known however which can ameliorate or suppress HF symptoms in certain patients.

HF is often coincident with one or more cardiac arrhythmia conditions, and thus some HF patients may be provided with a cardiac rhythm management device, such as an implantable pacemaker which may be combined with an implantable cardioverter defibrillator (ICD). For certain patients, appropriate multi-chamber low voltage pacing stimulation can improve cooperation between the multiple chambers of the heart and restore a degree of pumping effectiveness lost due to HF. ICDs provide relatively high energy/high voltage therapeutic shocks to interrupt episodes of fibrillation or to defibrillate the patient.

Pacing stimulations and defibrillation shocks are delivered via implanted electrodes which are arranged in contact with or near the patient's cardiac tissue. Electrodes can be positioned internally within the heart and such electrodes are often transvenously introduced. Electrodes can also be affixed in the exterior surface of the heart or configured as conductive external structures of implanted stimulation pulse generator/controller units. Surface electrodes have also been considered to apply stimulation to larger exterior surfaces of the patient's heart. Surface electrodes have proven difficult to implement as it has proven problematic to reliably maintain surface electrodes in a desired position over time. The heart exterior undergoes rather significant motion throughout the cardiac cycle and this motion tends to dislodge electrodes and electrode fixations positioned on the surface.

One further physiological characteristic of certain HF patients and one more commonly found in more severe conditions of HF is an excessive distension or dilation of the heart. The heart normally expands and contracts throughout the cardiac cycle about a median stable size. However, in certain patients as the HF progresses, the heart can become abnormally enlarged or dilated such that the overall size of the heart is greater than in a pre-disease normal condition. Unfortunately, this excessive dilation or distension strains and weakens the heart and reduces its pumping capacity, thus requiring even more exertion from the weakened diseased heart. The over-exertion of the heart required to maintain the pumping output of the heart can further weaken the cardiac tissue leading to further dilation or distention of the heart muscle in a positive feedback progression of the chronic HF condition.

One proposed therapy for HF patients experiencing heart dilation is to provide some sort of mechanical or structural support to the heart muscle to resist excessive enlargement of the heart. For example, a variety of structures known generally as cardiac constraints have been proposed to partially encompass the outer surface of the heart to limit excessive distention of a diseased heart. While such cardiac constraints do not halt the progression of the HF, it appears that in certain cases they may be able to offer benefits in limiting the progression of continued heart enlargement and weakening of the heart muscle during heart failure-based dilation.

SUMMARY

Certain embodiments described herein are based on combining structural support therapy with electrical rhythm management therapy. In certain embodiments, a mechanical support or cardiac constraint is provided to inhibit excessive distension or further enlargement of a diseased heart, such as in a HF patient. The cardiac constraint can be combined with an implantable cardiac stimulation device which automatically monitors the patient's cardiac activity and provides indicated therapeutic stimulation. In certain embodiments, the cardiac constraint facilitates use of relatively large area surface electrodes positioned on the external surface of the heart. The surface electrodes can be utilized to provide alternative stimulation therapy having advantages as compared to known transvenously implanted or more localized electrodes. Certain embodiments also facilitate further reduction in the volumetric envelope of implantable devices by revising therapy to allow use of smaller components, such as shocking capacitors.

Thus, one embodiment includes an implantable cardiac therapy appliance comprising a mechanical support structure configured to at least partially encompass a patient's heart so as to inhibit further enlargement of the heart during diastole and to allow substantially uninhibited systole, at least two separate pairs of surface electrodes arranged to define at least two stimulation paths intersecting between the electrodes, a stimulation pulse generator connectable to the at least two separate pairs of electrodes, and a controller receiving sensed signals from at least one of the electrodes and evaluating these signals for indications of cardiac arrhythmia and selectively inducing the stimulation pulse generator to generate and deliver indicated anti-tachycardia stimulations across the at least two stimulation paths.

DETAILED DESCRIPTION OF THE PREFERRED EMBODIMENT

Reference will now be made to the drawings wherein like numerals refer to like parts throughout. The following description is of the best mode presently contemplated for practicing the invention. This description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.

Figure 1:
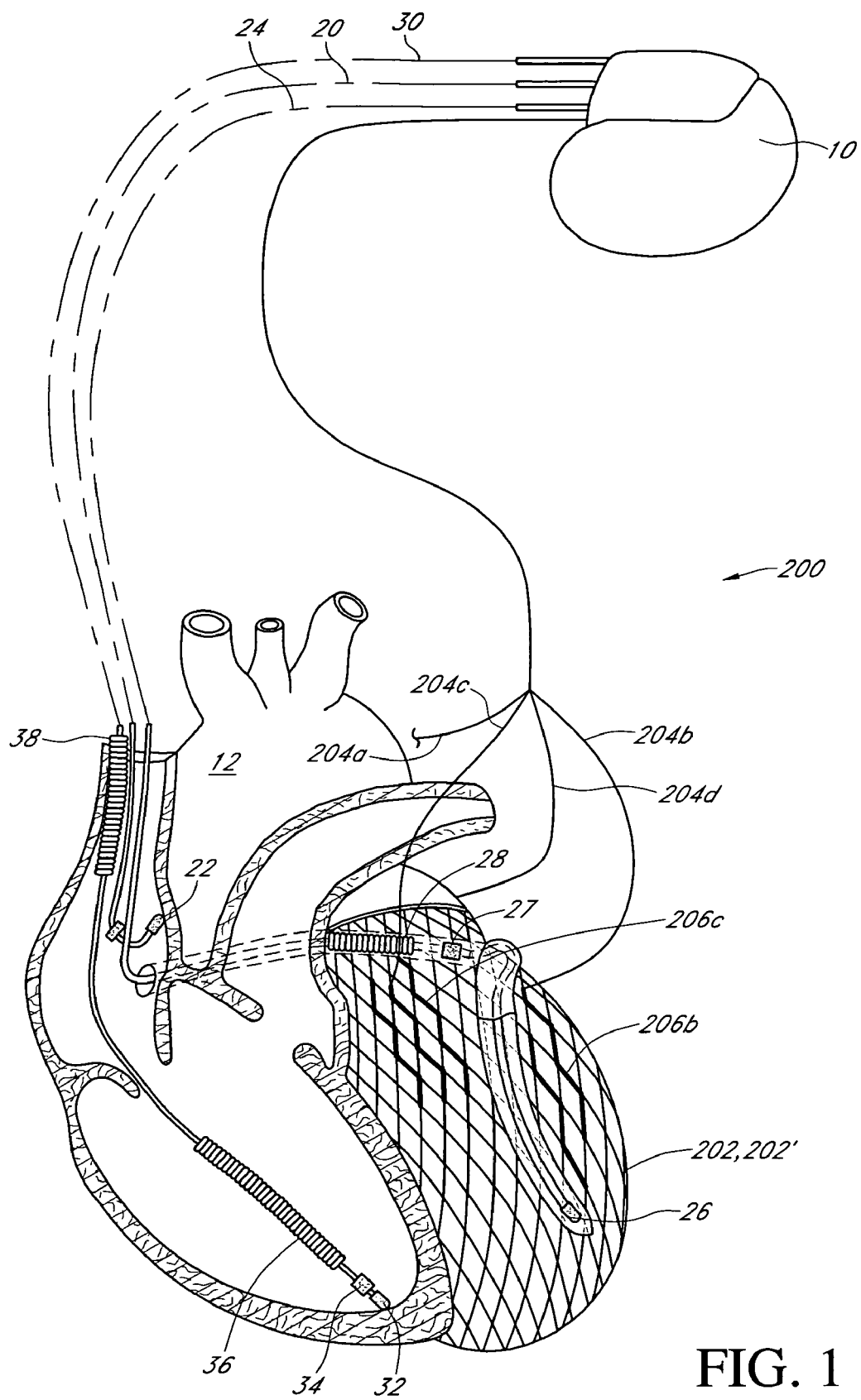
FIG. 1 is a simplified diagram illustrating a therapeutic appliance with an implantable stimulation device in electrical communication with at least three leads implanted into a patient's heart for delivering multi-chamber stimulation and shock therapy and a mechanical structural support to restrain excessive distension of the heart.

In one embodiment, as shown in FIG. 1, a therapeutic appliance 200 comprising an implantable cardiac stimulation device 10 is in electrical communication with a patient's heart 12 by way of three leads, 20, 24 and 30, suitable for delivering multi-chamber stimulation and shock therapy. To sense atrial cardiac signals and to provide right atrial chamber stimulation therapy, the stimulation device 10 is coupled to an implantable right atrial lead 20 having at least an atrial tip electrode 22, which typically is implanted in the patient's right atrial appendage.

To sense left atrial and ventricular cardiac signals and to provide left chamber pacing therapy, the stimulation device 10 is coupled to a "coronary sinus" lead 24 designed for placement in the "coronary sinus region" via the coronary sinus ostium (OS) for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, an exemplary coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28.

The stimulation device 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and a superior vena cava (SVC) coil electrode 38. Typically, the right ventricular lead 30 is transvenously inserted into the heart 12 so as to place the right ventricular tip electrode 32 in the right ventricular apex so that the RV coil electrode will be positioned in the right ventricle and the SVC coil electrode 38 will be positioned in the superior vena cava. Accordingly, the right ventricular lead 30 is capable of receiving cardiac signals, and delivering stimulation in the form of pacing and shock therapy to the right ventricle.

The device 10 is further in electrical communication with the heart via a surface electrode lead 204 and one or more surface electrodes 206. FIG. 1 illustrates one embodiment with four surface electrodes 206a, 206b, 206c, and 206d of which electrodes 206a and 206d are hidden from view. The electrodes 206a, 206b, 206c, and 206d are connected with corresponding lead sections 204a, 204b, 204c, and 204d. Further description of the function and structures of the leads 204a, 204b, 204c, and 204d and electrodes 206a, 206b, 206c, and 206d will follow below.

Figure 2:
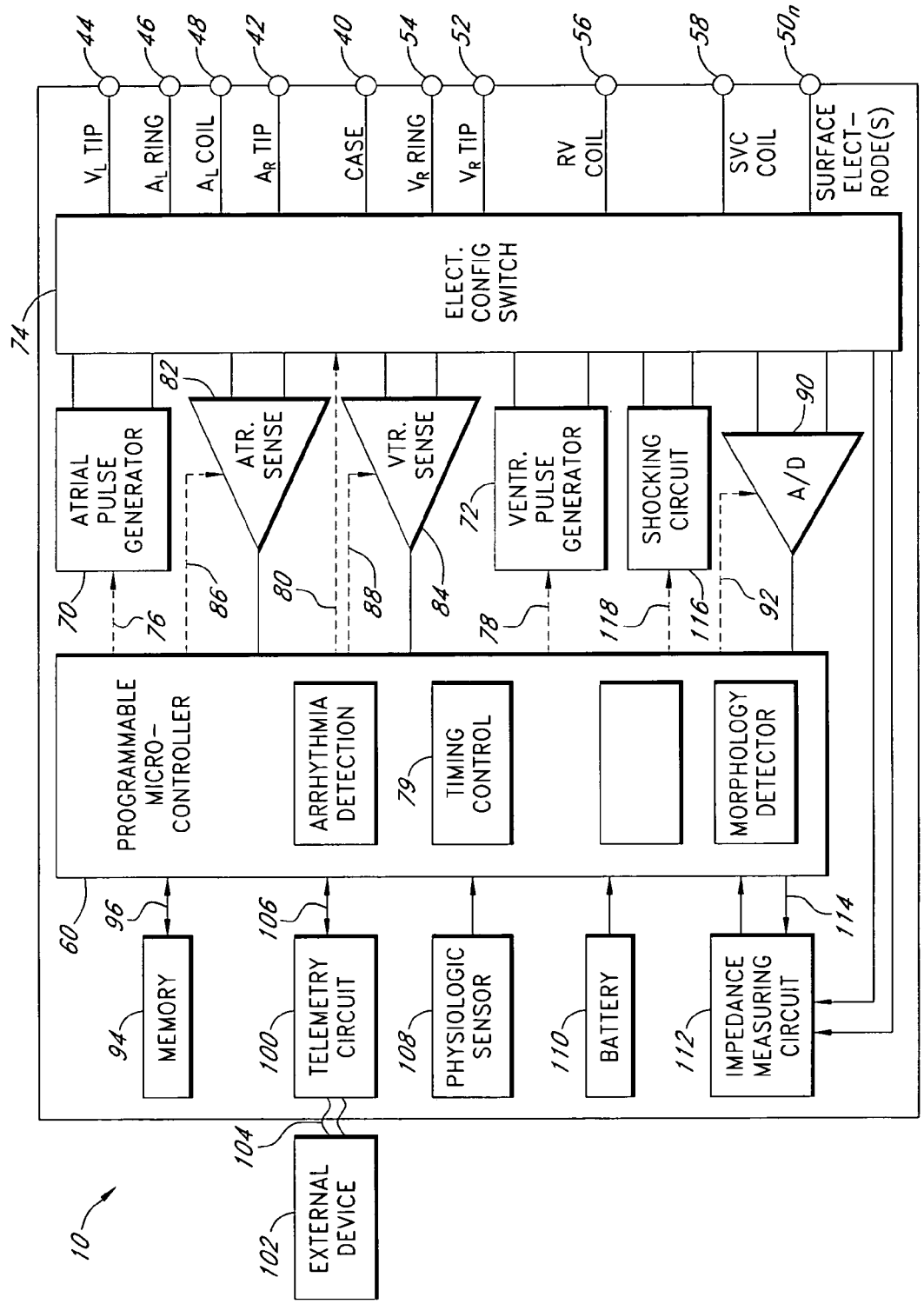
FIG. 2 is a functional block diagram of a multi-chamber implantable stimulation device illustrating the basic elements of a stimulation device which can provide cardioversion, defibrillation and pacing stimulation in four chambers of the heart.

As illustrated in FIG. 2, a simplified block diagram is shown of the multi-chamber implantable stimulation device 10, which is capable of treating both fast and slow arrhythmias with stimulation therapy, including cardioversion, defibrillation, and pacing stimulation. While a particular multi-chamber device 10 is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation.

The housing 40 for the stimulation device 10, shown schematically in FIG. 2, is often referred to as the "can", "case" or "case electrode" and may be programmably selected to act as the return electrode for all "unipolar" modes. The housing 40 may further be used as a return electrode alone or in combination with one or more of the coil electrodes, 28, 36 and 38, for shocking purposes. The housing 40 further includes a connector (not shown) having a plurality of terminals, 42, 44, 46, 48, $50_n$, 52, 54, 56, and 58 (shown schematically and, for convenience, the names of the electrodes to which they are connected are shown next to the terminals). As such, to achieve right atrial sensing and pacing, the connector includes at least a right atrial tip terminal ($A_R$ TIP) 42 adapted for connection to the atrial tip electrode 22.

To achieve left chamber sensing, pacing and shocking, the connector includes at least a left ventricular tip terminal ($V_L$ TIP) 44, a left atrial ring terminal ($A_L$ RING) 46, and a left atrial shocking terminal ($A_L$ COIL) 48, which are adapted for connection to the left ventricular tip electrode 26, the left atrial ring electrode 27, and the left atrial coil electrode 28, respectively.

The connector $50_n$ is configured to selectively connect to one or more of the leads 204 and the corresponding surface electrodes 206. The connector $50_n$ facilitates sensing, pacing, and shocking via the leads 204 and corresponding surface electrodes 206 in a manner similar to that of the other electrodes, however with differences that will be described in greater detail below.

To support right chamber sensing, pacing and shocking, the connector further includes a right ventricular tip terminal ($V_R$ TIP) 52, a right ventricular ring terminal ($V_R$ RING) 54, a right ventricular shocking terminal ($R_V$ COIL) 56, and an SVC shocking terminal (SVC COIL) 58, which are adapted for connection to the right ventricular tip electrode 32, right ventricular ring electrode 34, the RV coil electrode 36, and the SVC coil electrode 38, respectively.

At the core of the stimulation device 10 is a programmable microcontroller 60 which controls the various modes of stimulation therapy. As is well known in the art, the microcontroller 60 typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. The details of the design and operation of the microcontroller 60 are not critical to the invention. Rather, any suitable microcontroller 60 may be used that carries out the functions described herein. The use of microprocessor-based control circuits for performing timing and data analysis functions are well known in the art.

As shown in FIG. 2, an atrial pulse generator 70 and a ventricular pulse generator 72 generate pacing stimulation pulses for delivery by the right atrial lead 20, the right ventricular lead 30, and/or the coronary sinus lead 24 via an electrode configuration switch 74. It is understood that in order to provide stimulation therapy in each of the four chambers of the heart, the atrial and ventricular pulse generators, 70 and 72, may include dedicated, independent pulse generators, multiplexed pulse generators, or shared pulse generators. The pulse generators, 70 and 72, are controlled by the microcontroller 60 via appropriate control signals, 76 and 78, respectively, to trigger or inhibit the stimulation pulses.

The microcontroller 60 further includes timing control circuitry 79 which is used to control the timing of such stimulation pulses (e.g., pacing rate, atrio-ventricular (AV) delay, atrial interconduction (A-A) delay, or ventricular interconduction (V-V) delay, etc.) as well as to keep track of the timing of refractory periods, PVARP intervals, noise detection windows, evoked response windows, alert intervals, marker channel timing, etc., which is well known in the art.

The switch 74 includes a plurality of switches for connecting the desired electrodes to the appropriate I/O circuits, thereby providing complete electrode programmability. Accordingly, the switch 74, in response to a control signal 80 from the microcontroller 60, determines the polarity of the stimulation pulses (e.g., unipolar, bipolar, combipolar, etc.) by selectively closing the appropriate combination of switches (not shown) as is known in the art.

Atrial sensing circuits 82 and ventricular sensing circuits 84 may also be selectively coupled to the right atrial lead 20, coronary sinus lead 24, and the right ventricular lead 30, through the switch 74 for detecting the presence of cardiac activity in each of the four chambers of the heart. Accordingly, the atrial (ATR. SENSE) and ventricular (VTR. SENSE) sensing circuits, 82 and 84, may include dedicated sense amplifiers, multiplexed amplifiers, or shared amplifiers. The switch 74 determines the "sensing polarity" of the cardiac signal by selectively closing the appropriate switches, as is also known in the art. In this way, the clinician may program the sensing polarity independently of the stimulation polarity.

Each sensing circuit, 82 and 84, preferably employs one or more low power, precision amplifiers with programmable gain and/or automatic gain control, bandpass filtering, and a threshold detection circuit, as known in the art, to selectively sense the cardiac signal of interest. The automatic gain control enables the device 10 to deal effectively with the difficult problem of sensing the low amplitude signal characteristics of atrial or ventricular fibrillation. The outputs of the atrial and ventricular sensing circuits, 82 and 84, are connected to the microcontroller 60 which, in turn, are able to trigger or inhibit the atrial and ventricular pulse generators, 70 and 72, respectively, in a demand fashion in response to the absence or presence of cardiac activity in the appropriate chambers of the heart.

For arrhythmia detection, the device 10 utilizes the atrial and ventricular sensing circuits, 82 and 84, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation) are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to the inputs of an analog-to-digital (A/D) data acquisition system 90. The data acquisition system 90 is configured to acquire intracardiac electrogram (IEGM) signals, convert the raw analog data into a digital signal, and store the digital signals for later processing and/or telemetric transmission to an external device 102. The data acquisition system 90 is coupled to the right atrial lead 20, the coronary sinus lead 24, and the right ventricular lead 30 through the switch 74 to sample cardiac signals across any pair of desired electrodes.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 12 within each respective tier of therapy.

Advantageously, the operating parameters of the implantable device 10 may be non-invasively programmed into the memory 94 through a telemetry circuit 100 in telemetric communication with the external device 102, such as a programmer, transtelephonic transceiver, or a diagnostic system analyzer. The telemetry circuit 100 is activated by the microcontroller by a control signal 106. The telemetry circuit 100 advantageously allows IEGMs and status information relating to the operation of the device 10 (as contained in the microcontroller 60 or memory 94) to be sent to the external appliance 2002 through an established communication link 104.

In the preferred embodiment, the stimulation device 10 further includes a physiologic sensor 108, commonly referred to as a "rate-responsive" sensor because it is typically used to adjust pacing stimulation rate according to the exercise state of the patient. However, the physiological sensor 108 may further be used to detect changes in cardiac output, changes in the physiological condition of the heart, or diurnal changes in activity (e.g., detecting sleep and wake states). Accordingly, the microcontroller 60 responds by adjusting the various pacing parameters (such as rate, AV Delay, V-V Delay, etc.) at which the atrial and ventricular pulse generators, 70 and 72, generate stimulation pulses.

The stimulation device additionally includes a battery 110 which provides operating power to all of the circuits shown in FIG. 2. For the stimulation device 10, which employs shocking therapy, the battery 110 must be capable of operating at low current drains for long periods of time and then be capable of providing high-current pulses (for capacitor charging) when the patient requires a shock pulse. The battery 110 must also have a predictable discharge characteristic so that elective replacement time can be detected. Accordingly, embodiments of the device 10 including shocking capability preferably employ lithium/silver vanadium oxide batteries. For embodiments of the device 10 not including shocking capability, the battery 110 will preferably be lithium iodide or carbon monoflouride or a hybrid of the two.

As further shown in FIG. 2, the device 10 is shown as having an impedance measuring circuit 112 which is enabled by the microcontroller 60 via a control signal 114.

In the case where the stimulation device 10 is intended to operate as an implantable cardioverter/defibrillator (ICD) device, it must detect the occurrence of an arrhythmia and automatically apply an appropriate electrical shock therapy to the heart aimed at terminating the detected arrhythmia. To this end, the microcontroller 60 further controls a shocking circuit 116 by way of a control signal 118. The shocking circuit 116 generates shocking pulses of low (up to 0.5 joules), moderate (0.5-10 joules), or high energy (11 to 40 joules), as controlled by the microcontroller 60. Such shocking pulses are applied to the patient's heart 12 through at least two shocking electrodes, and as shown in this embodiment, selected from the left atrial coil electrode 28, the RV coil electrode 36, and/or the SVC coil electrode 38. As noted above, the housing 40 may act as an active electrode in combination with the RV electrode 36, or as part of a split electrical vector using the SVC coil electrode 38 or the left atrial coil electrode 28 (i.e., using the RV electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5-40 joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

Figure 3B:
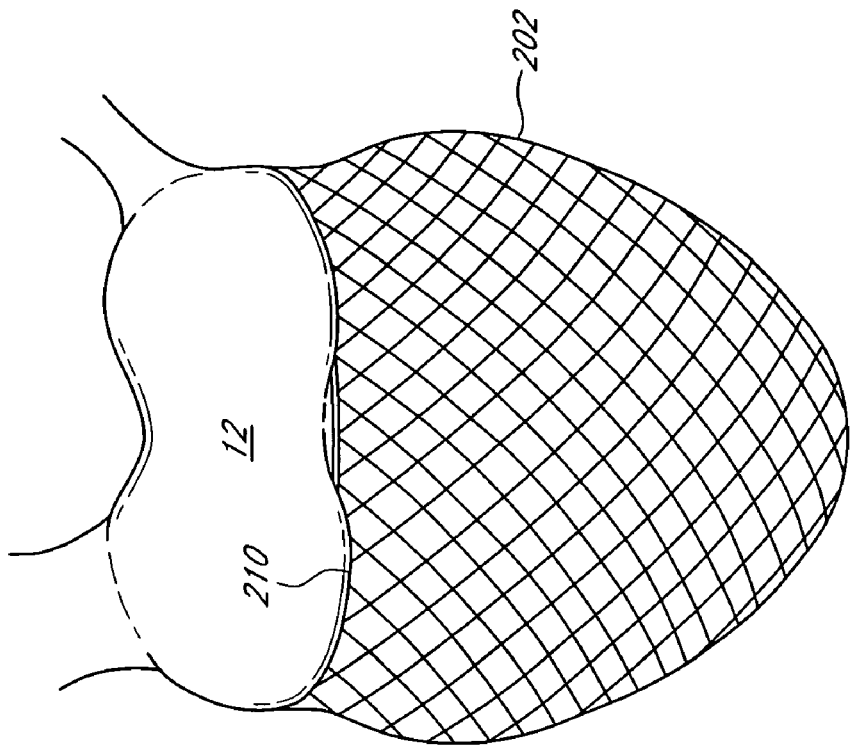
FIG. 3B illustrates the embodiment of cardiac constraint of FIG. 3A as applied to a patient's heart.
Figure 3A:
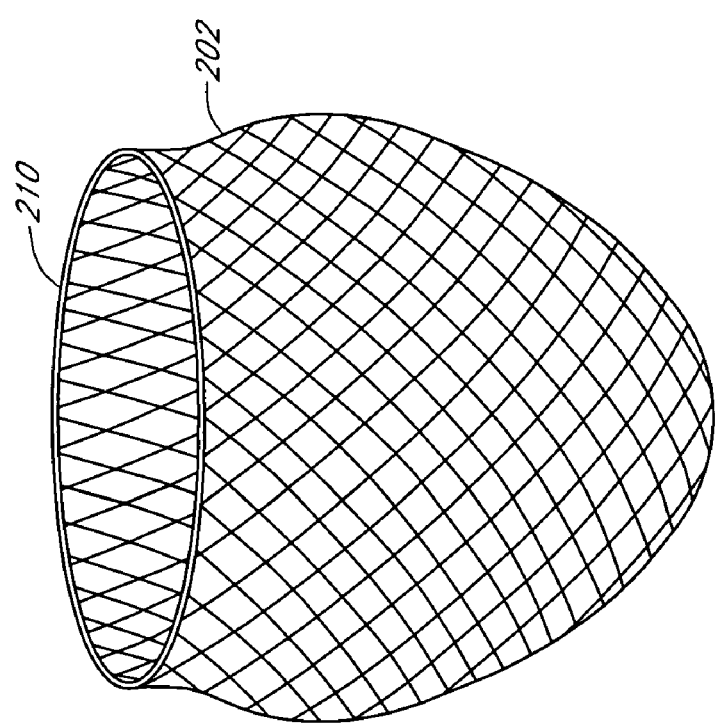
FIG. 3A illustrates in perspective view one embodiment of a cardiac constraint or mechanical support structure.
Figure 4B:
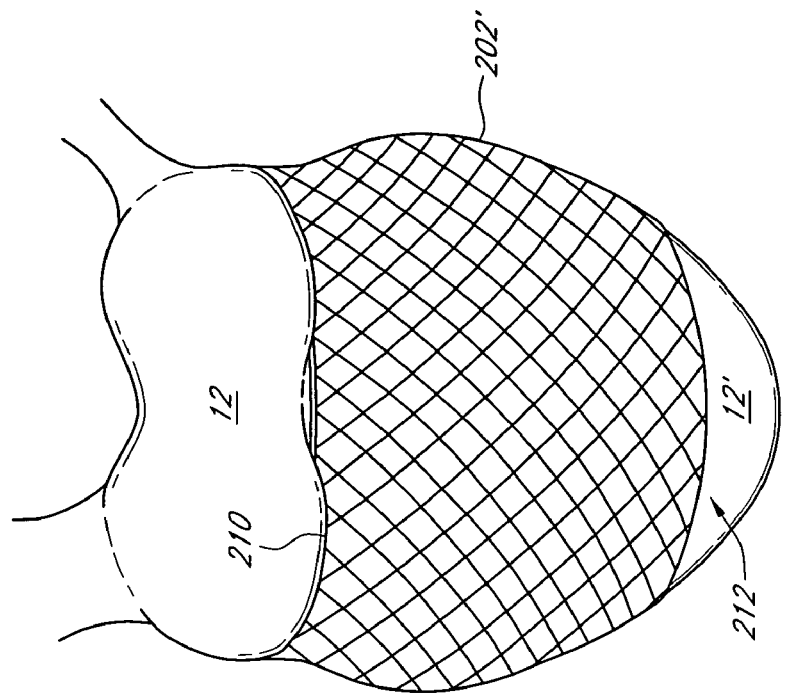
FIG. 4B illustrates the embodiment of FIG. 4A as applied to a patient's heart.
Figure 4A:
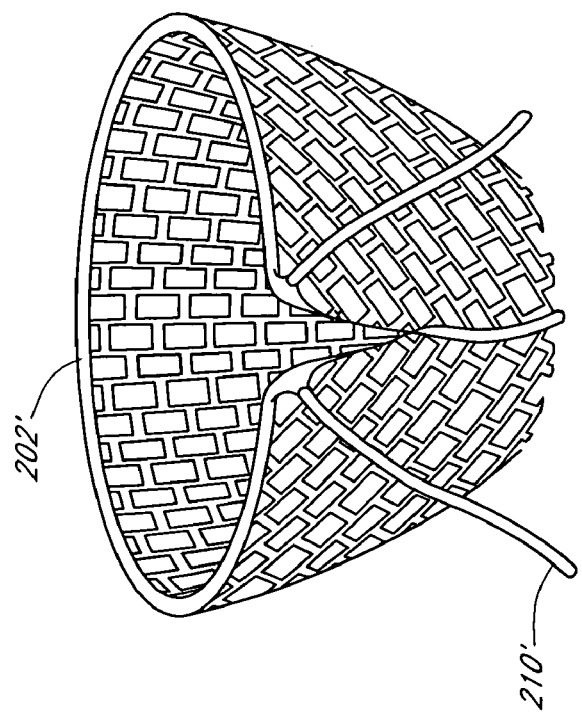
FIG. 4A illustrates another embodiment of cardiac constraint or mechanical support structure.

FIG. 1 also illustrates that the appliance 200 comprises a cardiac constraint 202, 202'. The cardiac constraint 202, 202' provides structural or mechanical support around at least a portion of the heart 12 to restrain or inhibit excessive distention or dilation of the heart 12, particularly in HF patients who may be experiencing weakening of the heart muscle. The cardiac constraint 202, 202' comprises a generally web-like or net structure which is interwoven to provide a distributed support structure around the exterior of the heart 12. In the embodiment illustrated in greater details in FIGS. 3A and 3B, a cardiac constraint 202 defines a generally cup or sack-shaped configuration. In this embodiment, the cardiac constraint 202 wraps around and encloses both a generally medially positioned horizontal circumference of the heart 12 as well as a lower end or apex of the heart 12. In another embodiment, as illustrated in FIGS. 4A and 4B, the cardiac constraint 202' defines generally a belt-like or girdle-shaped support structure. The cardiac constraint 202' would be positioned and secured generally about the medial horizontal circumference of the heart 12 and defines an opening 212 through which a lower portion or apex of the heart 12' extends.

In certain embodiments, the cardiac constraint or mechanical support structure 202, 202' is preferably comprised of a substantially inelastic material. In other embodiments, the cardiac constraint 202, 202' is resiliently contractible such that the constraint 202, 202' can maintain substantial contact with the heart 12 through expansion and contraction of the heart 12, while still inhibiting excessive distension or enlargement of the heart 12. Preferable materials for manufacturing the cardiac constraint 202, 202' are highly flexible and conformable to the exterior contour of the heart 12. It is also preferred that the cardiac constraint 202, 202' be formed at least partially of materials exhibiting very limited strain including elastic or inelastic strain. The materials used in forming the cardiac constraint 202, 202' should also preferably exhibit little to no hysteresis.

It is also preferable that the cardiac constraint 202, 202' be formed from material having relatively low coefficient of friction, as well as material that is relatively smooth and free of sharp edges, corners, and/or protrusions. As the cardiac constraint 202, 202' will be implanted in a position in contact with the exterior or epicardium of the heart 12, as well as with adjacent tissue, it is desirable that movement of the heart 12 against the cardiac constraint 202, 202', as well as induced movement of the cardiac constraint 202, 202' by the heart 12 avoid excessive abrasion or irritation of adjacent patient tissue. It will of course also be understood that the cardiac constraint 202, 202' need be formed of a material which is biocompatible and capable of being readily sterilized for implantation, such as by commonly used methods and systems, such as gamma ray radiation, ethylene oxide exposure, and/or steam sterilization.

The cardiac constraint 202, 202' is adapted to be secured in place around or over the exterior or epicardium of the heart 12 and to remain substantially in place throughout the cyclical contraction and relaxation of the heart 12. The cardiac constraint 202, 202' is preferably configured to relatively snugly conform to the external contour of the expanded heart 12. This allows the cardiac constraint 202, 202' to constrain or limit excessive distention or dilation of the heart during diastole while permitting substantially unimpeded contraction of the heart during a systole cycle.

The cardiac constraint 202, 202' in certain embodiments includes a dedicated securing structure 210 to assist in maintaining the cardiac constraint 202, 202' in the desired position on the exterior of the patient's heart 12. FIGS. 3A and 3B illustrate one embodiment of a securing structure 210 configured generally as a cinch or waist belt-type structure to secure the cardiac constraint 202 at an upper periphery to the patient's heart 12. FIGS. 4A and 4B illustrate another embodiment of securing structure 210' which in this embodiment includes both the cinch or waist belt aspect as in the securing structure 210 illustrated in FIGS. 3A and 3B as well as an adjustable or lace-type region. Thus, in this embodiment, the securing structure 210' can both cinch or secure an upper periphery of the cardiac constraint 202', as well as to provide an adjustable circumference or diameter of the cardiac constraint 202'. The securing structure 210', including the adjustable region, can be further utilized to adjust or conform a horizontal diameter or circumference of the cardiac constraint 202' to varying dimensions along a vertical extent of the cardiac constraint 202'.

Thus, the adjustment region of the securing structure 210' can be utilized to adjust the cardiac constraint 202' to a more strictly cylindrical contour, a more rounded or spherical contour, or other symmetric or asymmetric contour depending on the indications for a particular patient. While the appliance 200 would generally be provided in a variety of different sizes and contours to accommodate the needs of different individual patients, the adjustment feature of the securing structure 210' facilitates fine tuning of the fit of the cardiac constraint 202' to the particular contour of a given individual and also admits the possibility to adjust or refine the contour of the cardiac constraint 202' over time, for example, to accommodate changes in the size or shape of the patient's heart 12.

As also is shown in FIG. 1, one or more leads 204 extend from the device 10 to the cardiac constraint portion 202, 202' of the therapeutic appliance 200. The leads 204 connect the device 10 to corresponding one or more surface electrode assemblies 206. In one particular embodiment, four leads 204a-204d are connected to four corresponding surface electrode assemblies 206-206d. The surface electrodes 206 are distributed as generally planar electrode assemblies and in certain embodiments encompass a surface area on the order of several square centimeters. The electrode assemblies 206 are further configured to be positioned adjacent the outer surface of the patient's heart 12 and to be overlaid by the cardiac constraint 202, 202'. In certain embodiments, the electrode assemblies 206 are at least partially retained in place by the overlaid cardiac constraint 202, 202' and/or are incorporated within and positioned along an inner surface of the cardiac constraint 202, 202' as described in greater detail below. The surface electrodes 206 facilitate provision of therapeutic stimulation and in certain embodiments also sensing of signals from the outer surface of the patient's heart 12. In various embodiments of the invention, one or more surface electrodes 206 can apply therapeutic stimulation between pairs of individual surface electrodes 206 and/or between a surface electrode 206 and a conventionally arranged electrode, for example, an electrode arranged in the interior of the heart 12 or an electrode configured as a housing or can of the device 10.

Figure 5:
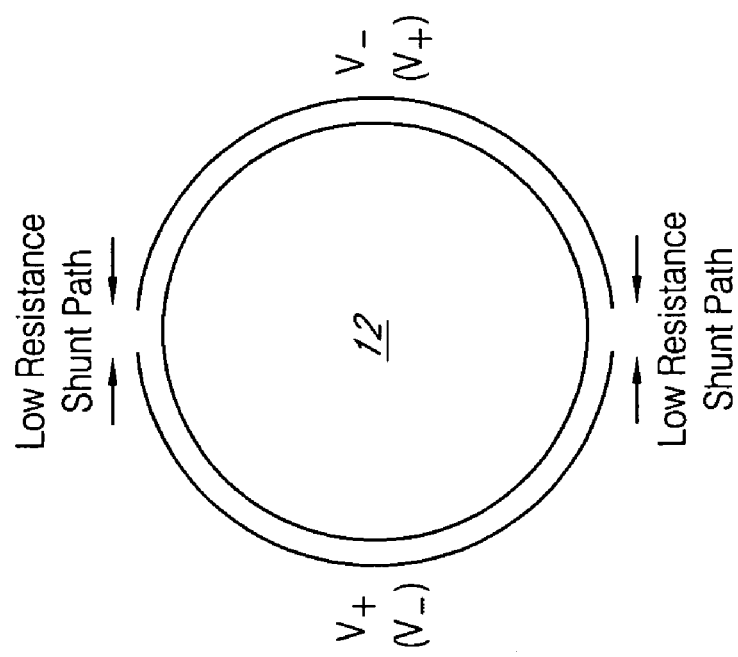
FIG. 5 is a schematic illustration of a prior art attempt to apply defibrillating shocks to a patient's heart via relatively large surface electrodes arranged about the exterior of a patient's heart and problems with this implementation.

FIG. 5 illustrates schematically one prior art attempt to apply therapeutic stimulations via large distributed surface electrodes. More particularly, FIG. 5 illustrates a previously attempted configuration for therapy delivery including opposed individual semi-cylindrical configured electrodes. The individual electrodes substantially encased or circumferentially encompassed the patient's heart. Thus, each individual electrode of this prior art attempt illustrated in FIG. 5 defines a substantially semi-cylindrical section such that together the two electrodes substantially completely encased a circumferential perimeter of the heart with relatively small gaps between adjacent ends of the individual electrodes.

A difficulty with this prior art configuration arises from the relatively close adjacency of opposed ends of the individual electrodes. As the electrodes themselves are relatively good conductors but the interposed cardiac tissue and blood contained with the heart is a comparatively poor conductor, relatively low resistant shunt paths are formed between opposed ends of each individual electrode, e.g., adjacent the narrow gaps between the ends of the opposed electrodes. Thus, a therapeutic stimulation applied between the opposed electrodes is substantially shunted along the low resistance shunt paths, such that a substantial portion of the heart does not receive a significant portion of the therapeutic stimulation energy. The tissue in the shunt path receives a disproportionately large portion of the energy. Thus, while relatively large surface areas of the heart can be exposed to the relatively high voltage of the therapeutic stimulation, current arising from this relatively high voltage which would desirably provide the therapeutic stimulation to the heart tissue substantially shunts around the heart and passes through the low resistance shunt path, effectively bypassing significant regions of the heart. Increasing or elongating the period of therapeutic stimulation is ineffective as higher intensity or longer duration stimulations simply results in increased current shunting along the low resistance shunt path which could even result in tissue damage from excessive current passing therethrough.

Figure 6:
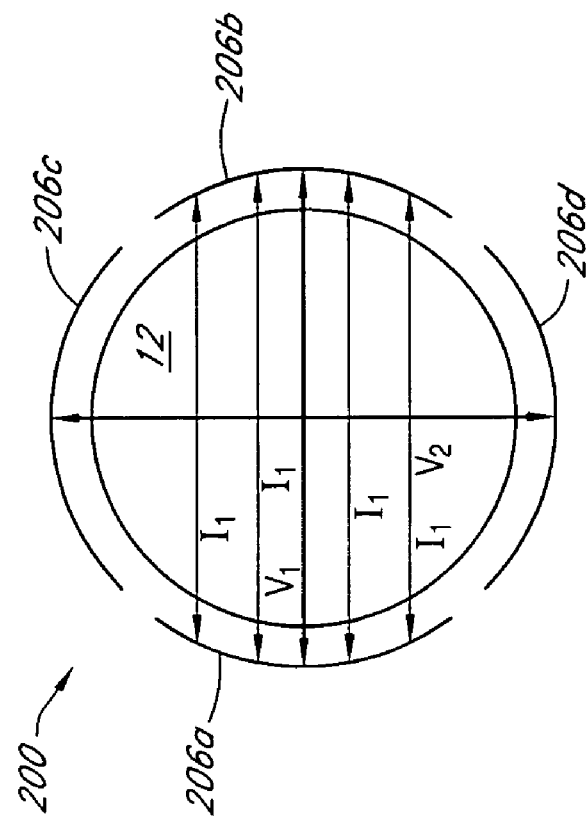
FIG. 6 illustrates schematically one embodiment of a system and method for applying cardiac stimulations, such as defibrillating shocks, in a manner which significantly reduces the problems and limitations associated with the prior art.

FIG. 6 illustrates one embodiment of an inventive system and method based on the appliance 200 of providing therapeutic stimulations with relatively large distributed or planar surface electrodes 206 which are capable of providing more effective therapy and avoid many of the difficulties with the prior art systems. In one embodiment, the appliance 200 comprises four individual surface electrode assemblies 206a-206d. First and second electrode assemblies 206a, 206b are arranged on the exterior surface of the patient's heart 12 and positioned substantially on opposite sides from each other. A third and fourth individual electrode assemblies 206c and 206d are also positioned on the surface of the patient's heart 12 and also positioned substantially opposite each other. In one embodiment, the first and second and third and fourth electrode assemblies 206a, 206b and 206c, 206d are arranged in quadrants in approximately 90° orientations.

As illustrated schematically in FIG. 6, spatial vectors $V_1$ and $V_2$ are defined between opposed pairs of the surface electrodes, e.g., between electrodes 206A and 206B and between electrodes 206C and 206D. FIG. 6 again illustrates schematically and in representative top section view relative arrangements of the electrode assemblies 206 with the patient's heart 12. While schematically illustrated as two-dimensional line segments, it will be understood that the spatial vectors $V_1$ and $V_2$ represent three-dimensionally spatially distributed vectors extending between the distributed or planar surfaces of the electrode assemblies 206. The spatial vectors extending between the opposed pairs of surface electrode assemblies 206 will thus intersect or overlap at regions between the opposed pairs of electrode assemblies 206, e.g., generally in the interior of the patient's heart 12.

Figure 7:
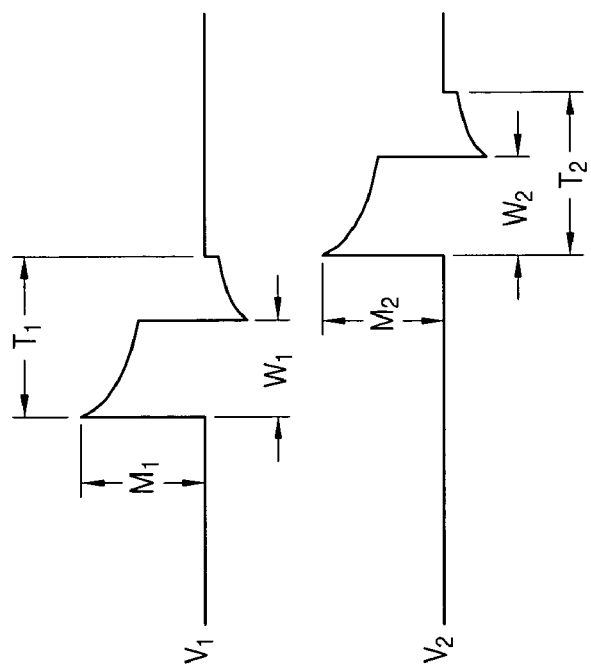
FIG. 7 illustrates schematically a representative stimulation wave-form which can be effectively utilized in combination with the embodiment illustrated by FIG. 6.

FIG. 7 illustrates schematically a representative therapeutic stimulation waveform which can be applied by the appliance 200 to the one or more surface electrodes 206. In one particular embodiment, the waveform indicated as $V_1$ is applied between the surface electrode assemblies 206A and 206B and similarly the therapeutic stimulation waveform indicated as $V_2$ is applied between the opposed pair of surface electrode assemblies 206C and 206D. As indicated in FIG. 7, the therapeutic stimulation waveforms $V_1$ and $V_2$ exhibit a peak magnitude $M_1$ and $M_2$, respectively. The therapeutic stimulation waveforms $V_1$ and $V_2$ exhibit generally the exponential decay of a capacitive discharge. The therapeutic waveforms $V_1$ and $V_2$ also exhibit truncation after a pulse width $W_1$ and $W_2$, respectively. Following the truncation after the initial pulse width $W_1$ and $W_2$, respectively, the therapeutic stimulation waveforms $V_1$ and $V_2$ reverse polarity to exhibit a biphasic stimulation waveform. A variety of particular therapeutic stimulation waveforms, for example, including defibrillation stimulation waveforms, will be well known and understood by one of ordinary skill. Further details can also be found in U.S. Pat. No. 5,540,721 to the inventor of the subject application. U.S. Pat. No. 5,540,721 is incorporated herein in its entirety by reference.

FIG. 7 also illustrates that in one embodiment the individual therapeutic stimulation waveforms $V_1$ and $V_2$ are separated in time such that at any given moment at most one of the therapeutic stimulation waveform $V_1$ or $V_2$ is active with the other waveform or both waveforms being quiescent. Thus, referring again to FIG. 6, at any given time, a therapeutic stimulation potential and corresponding current flow can exist between a single opposed pair of the surface electrode assemblies 206a, 206b, or 206c, 206d. As the interposed pair of surface electrode assemblies 206c, 206d, or 206a, 206b, respectively, are quiescent, a relatively spatially homogeneous current flow will arise between the opposed pairs of active surface electrode assemblies 206.

The configuration and placement of each of the electrode assemblies 206a-206d is preferably arranged such that electrode assemblies interposed between an active pair of electrode assemblies 206, does not present a low resistance shunt path between the active pair of electrode assemblies 206. For example, a gap or spacing between adjacent electrode assemblies 206a-206d is preferably maintained such that current resulting from the application of the therapeutic stimulation waveforms $V_1$ and $V_2$ is not provided with a substantial current shunt path between opposed pairs of electrode assemblies 206 through one or more adjacent interposed electrode assemblies 206. This could otherwise result in shunting of the therapeutic current rising from the therapeutic stimulation waveforms $V_1$ and $V_2$ and ineffectually bypassing a substantial portion of the patient's heart 12 thereby compromising the therapeutic effects of the appliance 200.

A further advantage of this embodiment of the appliance 200 is that the electrode assemblies 206 are configured as relatively large area or distributed surface electrodes which are positioned substantially on opposite sides of the exterior of the patient's heart 12. This results in a plurality of spatially distributed point-to-point stimulation paths between opposed points of the individual electrode assemblies 206 that are approximately diameters passing generally through a virtual center of the patient's heart 12 or approximately chords passing near a virtual center of the patient's heart 12. As the surface electrode assemblies 206 are highly conductive, they will define substantially equipotential circuit nodes. This will result in relatively highly homogeneous potential fields between the opposed pairs of surface electrode assemblies 206. These relatively highly homogeneous potential fields will result in relatively homogenous current densities between the opposed pairs of surface electrodes 206. This aspect will give relatively low defibrillation thresholds as the defibrillation energy will be more efficiently distributed across the patient's heart 12. This aspect will also facilitate defibrillation with relatively small capacitors which will facilitate reduction in size of the physical envelope for the appliance 200.

Figure 8:
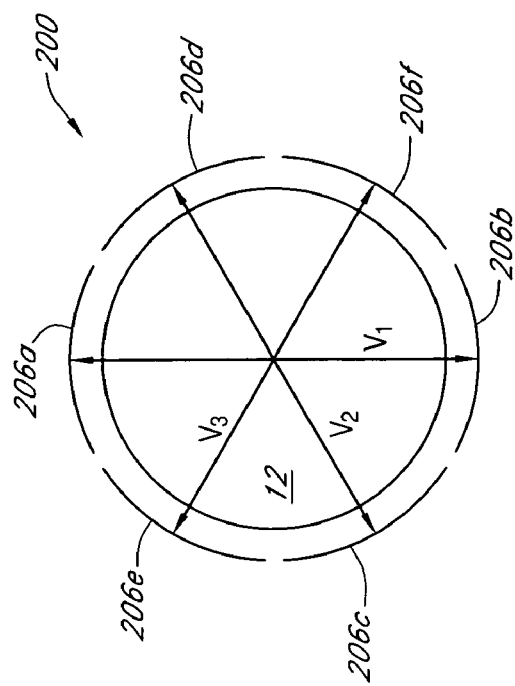
FIG. 8 illustrates schematically a further embodiment of a system and method for applying therapeutic stimulations to a patient's heart.
Figure 9:
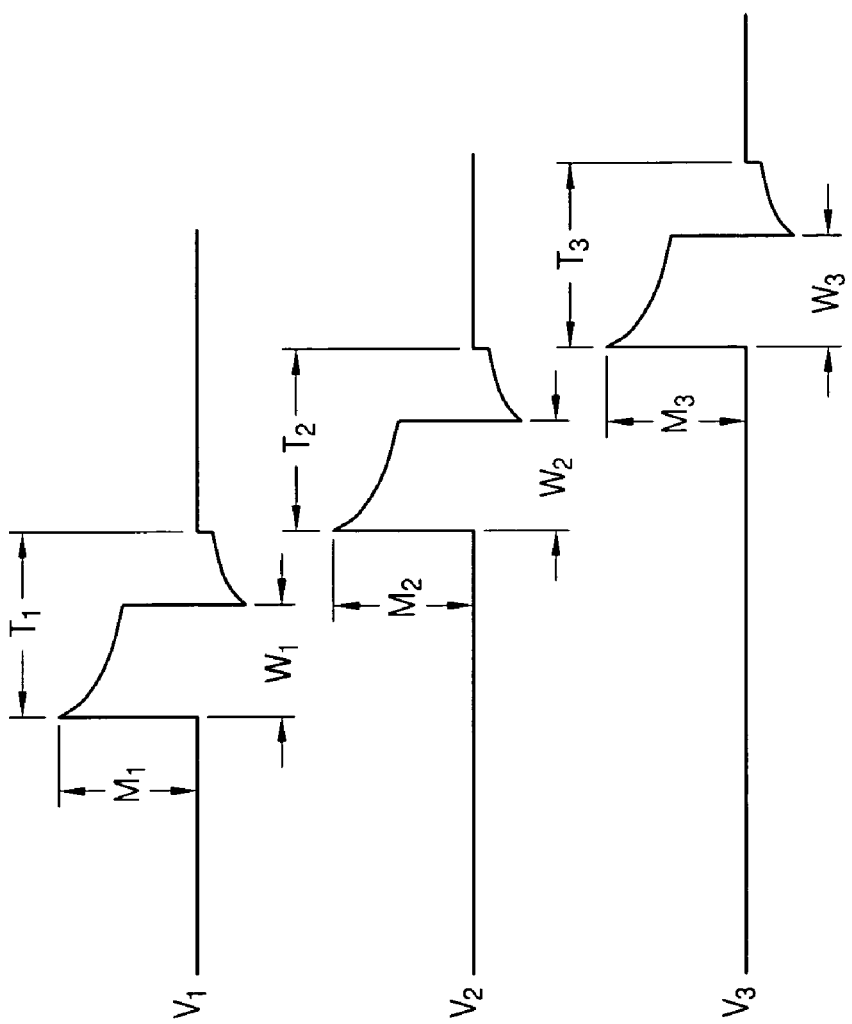
FIG. 9 illustrates schematically representative wave-forms of therapeutic stimulations which can be effectively applied in combination with the embodiment illustrated in FIG. 8.

FIGS. 8 and 9 illustrate a further embodiment of the therapeutic appliance 200 in this embodiment comprising an additional pair of individual surface electrode assemblies 206e and 206f. In this embodiment, each of the surface electrode assemblies 206a, 206b, 206c, 206d, 206e, 206f is arranged generally in sextiles uniformly about the circumference of the patient's heart 12. Thus, in this embodiment, a single electrode assembly 206 is arranged approximately every 60° about the periphery of the patient's heart 12. Again, as in FIG. 6, FIG. 8 is a schematic representation of a representative horizontal cross-section and the actual surface electrode assemblies 206 with the resulting stimulation vectors $V_1$, $V_2$ and $V_3$ existing therebetween would be vertically distributed so as to define spatial vectors extending three-dimensionally in space.

FIG. 9 illustrates schematically that, in this embodiment, the therapeutic appliance 200 additionally provides a third therapeutic stimulation waveform indicated $V_3$ which is also isolated in time with respect to the first and second therapeutic stimulation waveforms $V_1$ and $V_2$. Thus, in the embodiment of appliance 200 illustrated in FIGS. 8 and 9, three independent pairs of opposed surface electrodes 206 would receive independently corresponding therapeutic stimulation waveforms $V_1$, $V_2$, or $V_3$ each of which is isolated in time from the other two therapeutic stimulation waveforms such that at any given time, at most one of the opposed pairs of surface electrode assemblies 206 is actively provided with a therapeutic stimulation waveform $V_1$, $V_2$, $V_3$ with the remaining pairs of surface electrode assemblies 206 being quiescent.

This embodiment has the three waveforms $V_1$, $V_2$, $V_3$ each delivering their positive and negative phases before the next waveform. In another embodiment, the positive phases, such as three positive phases, appear in a sequence followed by the negative phases. Other variations of interleaving the positive and negative phases can be utilized in alternative implementations. However it is preferred that a larger positive phase initiates the sequence and is followed by paired negative phases within approximately 3 to 10 milliseconds.

Figure 10:
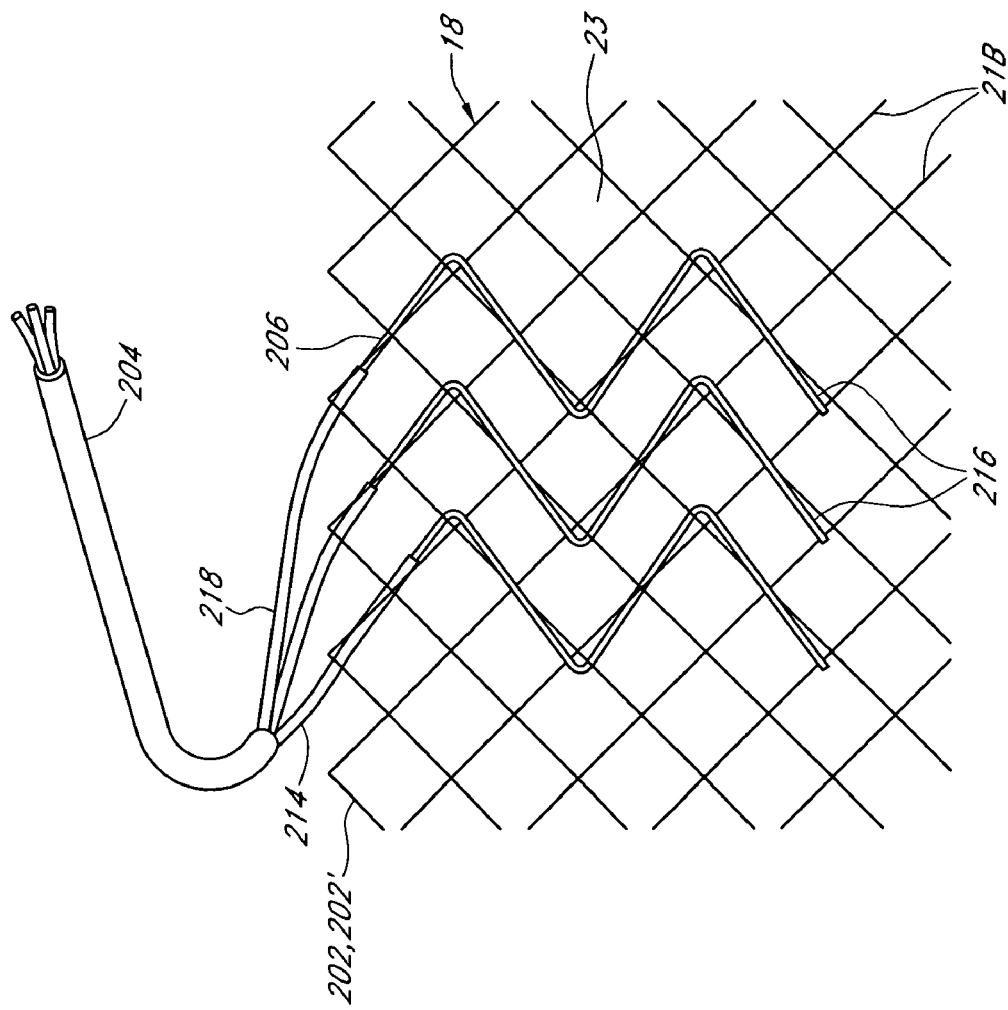
FIG. 10 illustrates one embodiment of a distributed or relatively large area electrode assembly which can be effectively utilized to apply therapeutic stimulations in combination with structural or mechanical support to a patient's heart.

FIG. 10 illustrates in greater detail one embodiment of a lead 204 and a surface electrode assembly 206. In this embodiment, the lead 204 comprises one or more individual conductors 214. Each conductor 214 comprises an interiorly disposed electrically conductive member surrounded or encompassed with an insulation material. A terminal or distal end of each of the one or more individual conductors 214 has the insulation removed so as to define an exposed portion 216 wherein the interior conductive member is exposed. Thus, a terminal or distal end of each inductor comprises an exposed portion 216 with the remainder covered with the insulating material so as to define an insulated portion 218 arranged generally proximally with respect to the device 10. In this embodiment, a distal or terminal portion of the individual conductors 214 and more particularly the exposed portions 216 thereof, are interwoven with or otherwise attached to the mesh or net material of the cardiac constraint 202, 202'. The exposed portions 216 are arranged generally on an interior surface of the cardiac constraint 202, 202' such that when the cardiac constraint 202, 202' is applied or affixed to the patient's heart 12, the exposed portions 216 of the conductors 214 are positioned and maintained in contact with the exterior or epicardium of the patient's heart 12. In one embodiment, as illustrated in FIG. 10, three individual conductors 214 have a portion of the insulative material removed to define three individual exposed portions 216 of the respective conductors 214.

The exposed portions 216 are arranged in a both vertically and horizontally extending and alternating diagonal pattern to form a zigzag or herringbone type weave along an interior region of the cardiac constraint 202, 202'. Thus, the exposed portions 216 of the conductors 214 define the distributed or surface electrode assembly 206. As previously noted, the materials of the cardiac constraint 202, 202', as well as of the lead 204 and conductors 214 thereof are preferably formed of a durable biocompatible material. Thus, the exposed portions 216 also preferably comprise a material that is both electrically conductive and biocompatible. The exposed portions 216 are also preferably formed in a manner which avoids sharp edges, roughness, or other surface features or contours which would likely lead to injury or irritation of the patient tissue in an implanted state.

Figure 11:
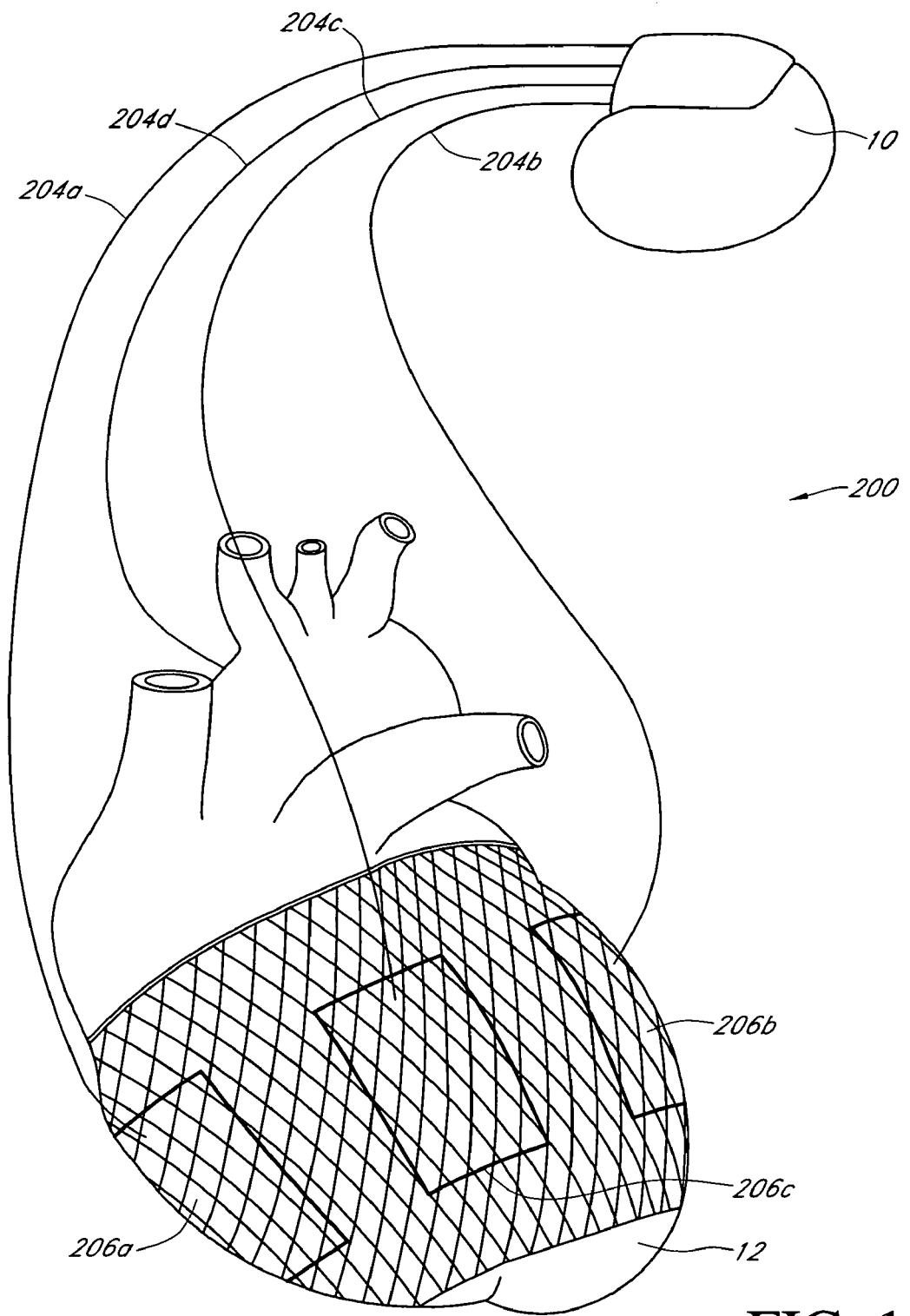
FIG. 11 illustrates another embodiment of distributed or relatively large area surface electrodes which can be utilized to apply therapeutic stimulation in combination with mechanical or structural support to a patient's heart.

FIG. 11 illustrates a further implementation or configuration of surface electrode assembly 206. In this embodiment, one or more surface electrode assemblies 206 are configured as generally rectangular continuous planar or sheet-like members comprising electrically conductive and biocompatible material. The one or more electrode assemblies 206 are positioned between the cardiac constraint 202, 202' and the outer surface of the patient's heart 12. Depending on the indications of a particular application and the particular configuration of the cardiac constraint 202, 202', the one or more surface electrode assemblies 206 can be simply maintained in place by the overlying pressure of the cardiac constraint 202, 202'. The one or more surface electrode assemblies 206 may also be attached to the cardiac constraint 202, 202' to be maintained in position or may be secured directly to the exterior surface of the patient's heart 12 in a variety of known manners. The one or more surface electrode assemblies 206 is a generally materially continuous planar member, however, may include a plurality of perforations or holes to facilitate gas and liquid exchange with the surface of the patient's heart 12.

Figure 12:
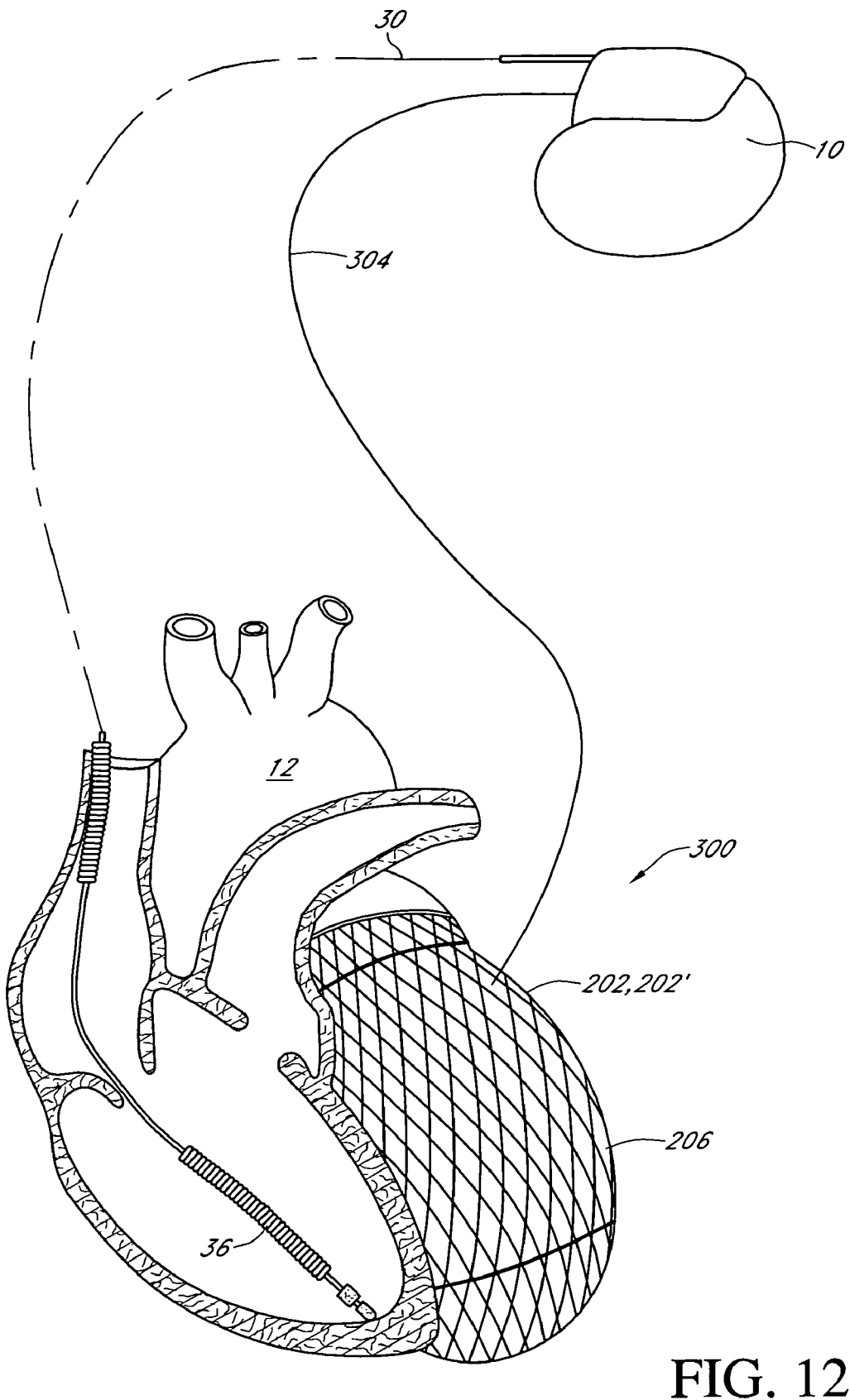
FIG. 12 illustrates a further embodiment of a distributed or relatively large area surface electrode assembly which can be utilized to apply therapeutic stimulation in combination with mechanical or structural support to a patient's heart.

FIG. 12 illustrates another embodiment of a therapeutic appliance 300 which includes several of the structural components and operational characteristics previously described for the therapeutic appliance 200. For example, the therapeutic appliance 300 would include the implantable stimulation device 10 and cardiac constraint 202, 202' substantially as previously described. The therapeutic appliance 300 also comprises one or more sensing/stimulation electrodes which are configured to be arranged in the interior of the patient's heart 12. In one particular embodiment, the therapeutic appliance 300 includes the RV coil electrode 36 which is configured for placement in the patient's right ventricle (RV).

The therapeutic appliance 300 also comprises one or more surface electrode assembly(ies) 206 which is/are configured to substantially circumferentially encompass an outer periphery of the patient's heart 12. In one embodiment, the surface electrode 206 is configured as a materially continuous single member which completely encircles or encompasses a periphery of the patient's heart 12. In another embodiment, the surface electrode assembly 206 comprises a distributed or sheet-like member which wraps substantially around the periphery of the patient's heart 12, however, may include a gap or void between opposed adjacent ends of the surface electrode 206 such that these opposed ends may not completely meet. The surface electrode 206 thus need not extend completely around the periphery of the patient's heart 12. In yet another embodiment, a plurality of individual surface electrodes 206, such as the electrodes 206a, 206b, 206c, and 206d can be electrically coupled to form a single electrical circuit node or electrode 206. In one embodiment, the switch 74 can commonly connect the individual electrodes 206a, 206b, 206c, and 206d, such as via the connector $50_n$ and lead 204. It will be understood that adjustment of the size of the cardiac constraint 202, 202' can vary the size of a gap or gaps between adjacent ends of a single surface electrode 206 or between adjacent individual electrodes 206.

A lead 304 connects the surface electrode 206 with the appliance 300 in a manner substantially similar to that previously described for the leads 204. The cardiac constraint 202, 202' maintains the surface electrode 206 in position either by overlying the electrode 206 or by providing an attachment surface. The constraint 202, 202' is configured to accommodate the cyclic contraction and relaxation of the heart 12 and thus can assist retaining the electrode 206 in position over an extended duration. This allows the appliance 200 to provide a therapeutic stimulation waveform between the interiorly positioned electrode 36 and the surface electrode 206.

Thus, the surface electrode 206 will define a generally cylindrical surface arranged about the outer surface of the patient's heart 12, and the RV coil electrode 36 will be positioned approximately along the centerline of a cylindrical surface defined by the surface electrode assembly 206. Thus, as one electrode, e.g., the surface electrode 206, defines a generally cylindrical surface with another electrode, e.g., the RV coil electrode 36 positioned approximately at a center of the cylinder, therapeutic stimulation waveforms applied between these two electrodes will result in relatively homogenous and radially uniform electric potentials and associated current densities. A more detailed quantitative analysis of an approximation of the operational characteristics of this embodiment of the therapeutic appliance 300 will follow with reference to FIG. 13.

Figure 13:
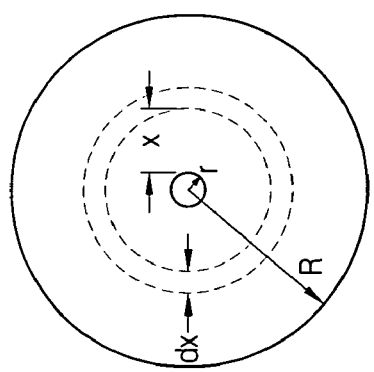
FIG. 13 illustrates an approximation model for determining appropriate device parameters for providing therapy according to embodiments of the invention.
Figure 13:
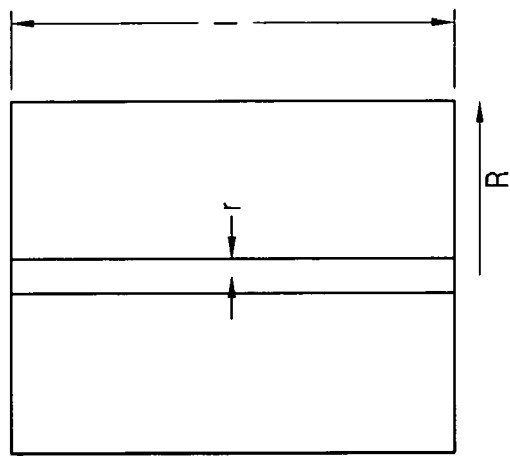

More particularly, FIG. 13 illustrates schematically in top and side views a cylindrical structure comprised of an outer cylinder which in this embodiment corresponds to the surface electrode assembly 206 and an inner catheter structure corresponding in this embodiment to the RV coil electrode 36. As illustrated in FIG. 13, in this approximation, the inner catheter structure is positioned along a centerline of the outer cylinder structure. The inner catheter structure has a radius r and the outer cylindrical structure has a radius R. The outer cylinder also has a length or height indicated as L.

Current flow between the electrically conductive outer cylindrical structure and the inner catheter structure will be determined both by the applied electrical potentials, as well as the impedance characteristics between these two conductive elements. In order to determine an estimate of the impedance characteristics, the outer cylindrical structure will be considered as a true cylinder, as well as the inner catheter structure. It will be understood that the following illustrative calculation is an approximation. Should a more precise estimate be desired, such a calculation will be well within the capabilities of a person of ordinary skill and could of course be further facilitated by use of computer-assisted modeling. The impedance between the outer cylinder and inner catheter structure will be calculated as a sum of thin cylindrical shells extending between the inner catheter structure and the outer cylinder having wall thicknesses of dx. Thus, each cylindrical shell or element has a resistance=

$$\frac{\rho dx}{2\pi x \ell}.$$

Thus the total resistance between the inner catheter structure and the outer cylinder is given by the integral from r to R of these individual cylindrical shell elements. Thus, the total resistance $$Z = \int_r^R \frac{\rho dx}{2\pi x \ell} = \frac{\rho}{2\pi \ell} \log e\left(\frac{R}{r}\right).$$

For representative values of ρ=150 Ω·cm, R=2 cm, ℓ=5 cm, and r=3 mm or corresponding to a 9 French lead gives a value of Z=approximately 9.1Ω.

Conventional implantable pacemaker/ICD devices are configured to deliver stimulations into load impedances of approximately 40Ω. If a conventional configuration of ICD were to be connected to an impedance of only 9.1Ω, it would be expected that such a conventional ICD would either suffer damage from delivering a shock into such a low impedance or would treat the impedance as a short circuit and inhibit delivery of a shock. However, even if a conventional ICD were to be able to successfully deliver a shock into a 9.1Ω load, the resulting stimulation pulses would be so narrow that it is highly unlikely that such shocks would have the desired therapeutic effect. According to aspects of the invention described in greater detail below, embodiments of the device 10, components thereof, and parameters of developed therapy are appropriately designed to successfully deliver stimulation to such an electrode configuration, e.g. one having a low impedance of approximately 9.1 Ω.

Figure 14:
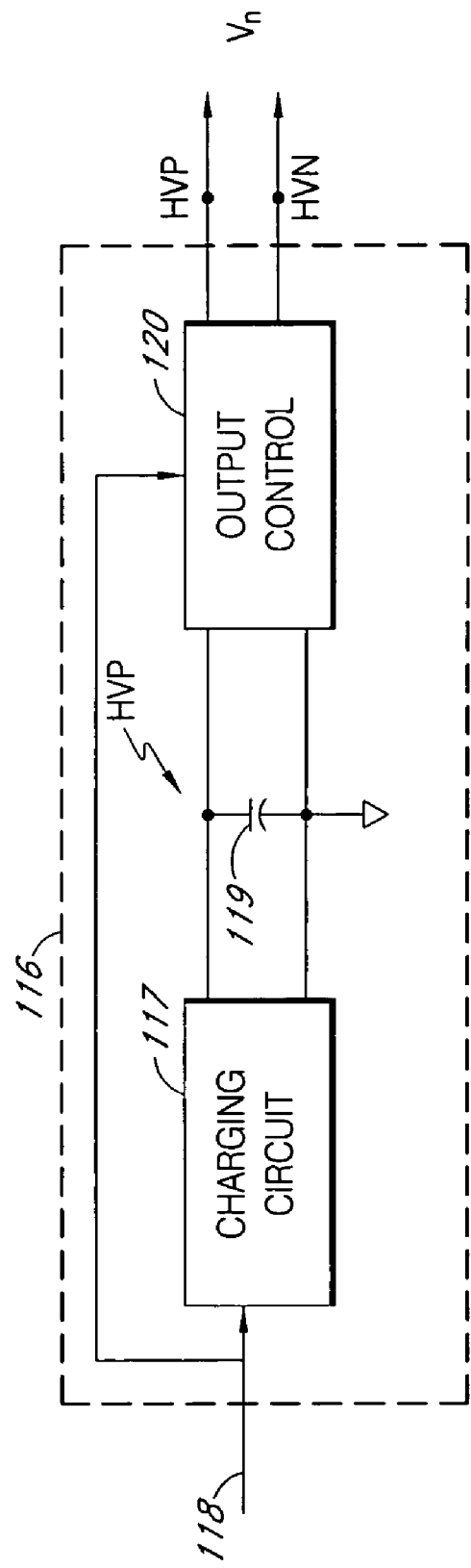
FIG. 14 is a block circuit diagram of one embodiment of a shocking circuit for developing and delivering therapy according to embodiments of the invention.

FIG. 14 is a high level block diagram illustrating one embodiment of a shocking circuit 116 of the device 10. As previously described, in one embodiment a control signal 118 is generated by the microcontroller 60 to regulate the generation and delivery of a therapeutic shock. The shocking circuit 116 generally includes a charging circuit 117 and an output control circuit 120. The output circuit 116 further includes charge storage 119, such as one or more high voltage capacitor(s), for temporary intermediate storage of the shocking energy. The charging circuit 117 may be of a type well known in the art for charging the charge storage 119 to a desired level. Once the charge storage 119 is charged, under control of the control signal 118, a relatively high-potential output voltage (HVP-HVN) will reside across the charge storage 119. This stored voltage is controlled by the output control 120 to produce a stimulation output having a desired waveform, such as the previously described stimulation waveforms $V_1$ and $V_2$. Additional details of embodiments of shocking circuits suitable for use with the embodiments of the invention described herein can be found in the co-owned U.S. application entitled "Implantable Cardiac Stimulation Device Including an Output Circuit that Provides Arbitrarily Shaped Defibrillation Waveforms", Ser. No. 10/687,386, filed Oct. 15, 2003 which is incorporated herein in its entirety.

Previously disclosed modeling (Kroll, M W., "A Minimal Model of the Monophasic Defibrillation Pulse" Pacing Clin. Electrophysiol. 1993 April; 16(4 Pt. 1):769-777) which reference is incorporated herein in its entirety by reference shows that in an ICD system, the charge storage 119 capacitance times the resistance or load impedance of the shock should be approximately 3 milliseconds. Solving for a load impedance of approximately 9.1 Ω gives a capacitance for the charge storage 119 of between about 200 and about 400 μF with a more preferable capacitance of approximately 300 microfarads. A typical maximum energy shock with current conventional ICDs delivers approximately 800 volts into a 40Ω resistance for a peak current of approximately 20 amperes. For an approximately 10Ω resistance, this would indicate a therapeutic shock of 360 to 100 V and more preferably a shock of approximately 200 volts or approximately 20 A at 10Ω.

Thus, in this embodiment of the therapeutic appliance 300, a more preferable capacitor for the charge storage 119 of the appliance 300 would be a 200 volt, 300 microfarad capacitor. Such a capacitor can be advantageously implemented in tantalum capacitors which have otherwise not worked out well for prior conventional type ICD systems as their voltages were too low for the most efficient defibrillation. An additional advantage of the therapeutic appliance 300 is that when employing charge storage 119 in the range of 200-400 μF at 100-360V, the total stored energy would be in the range of approximately 1-26 joule. With the more preferred charge storage 119 of approximately 200 volts and of 300 microfarad capacity, the total stored energy would be approximately 6 joules. This can be achieved with a capacitor substantially smaller than capacitors used in existing conventional type ICD systems.

The therapeutic stimulation wave forms employed with the appliance 300 can include morphologies similar to that previously illustrated with respect to the therapeutic stimulation wave forms $V_1$, $V_2$, $V_3$, as well as any of a number of other known therapeutic stimulation wave forms which will be well understood by one of ordinary skill in the art. The use of known conventional waveforms is facilitated in certain embodiments of the invention because the time constant of the delivered shock is kept close to conventional time constants by the above-described judicious choice of the capacitor value. Thus, existing well developed therapeutic stimulation wave form theories and evaluations can be readily carried over for implementation in the embodiment of therapeutic appliance 300 as described. Thus, in one particular embodiment, the total duration $T_n$ (FIGS. 7 and 9) of the therapeutic stimulation wave form would be biphasic and of less than approximately 15 ms. A more preferable waveform would comprise approximately 3-6 milliseconds for the first phase ($W_n$) and 2-3 milliseconds for the second phase of a biphasic stimulation wave form.

Although the above disclosed embodiments of the present teachings have been described, it should be understood that various omissions, substitutions, and changes in the form of the detail of the devices, systems and/or methods illustrated may be made by those skilled in the art without departing from the scope of the present teachings. Consequently, the scope of the invention should not be limited to the foregoing description but should be defined by the appended claims.

What is claimed is:

1. An implantable cardiac therapy appliance comprising:
   a mechanical support comprising a flexible structure configured to conform to an outer contour of a patient's heart and provide structural support at least during diastole to resist further distension of the heart, wherein the mechanical support is adjustable in circumference;
   a first electrode arranged on an inner surface of the support and configured to substantially circumferentially contact an outer surface of the patient's heart, wherein the first electrode comprises an exposed wire conductor portion arranged in a both a vertically and horizontally extending and alternating diagonal pattern with respect to the mechanical support and has opposite ends defining a gap, such that the size of the gap varies depending on the adjustment of the mechanical support;
   a second electrode configured to be implanted within an interior of the patient's heart; and
   a cardiac stimulation device wherein the stimulation device automatically monitors the heart for indications of fibrillation and, upon determining indications of fibrillation, selectively provides a defibrillation stimulation in the range of 100 to 360 volts between the first and second electrodes.

2. The appliance of claim 1, wherein the first electrode is comprised of a plurality of individual electrodes which are electrically coupled together to define the first electrode.

3. The appliance of claim 1, wherein the defibrillation stimulation is provided as a biphasic waveform of less than 15 ms total duration.

4. An implantable cardiac therapy appliance comprising:
a mechanical support comprising a flexible structure configured to conform to an outer contour of a patient's heart and to provide structural support at least during diastole to resist further distension of the heart, wherein the mechanical support is adjustable in circumference;
a first electrode arranged on an inner surface of the support and configured to substantially circumferentially contact an outer surface of the patient's heart, wherein the first electrode comprises an exposed conductor portion arranged in a both a vertically and horizontally extending and alternating diagonal pattern with respect to the mechanical support and has opposite ends defining a gap, such that the size of the gap varies depending on the adjustment of the mechanical support;
a second electrode configured to be implanted within an interior of the patient's heart; and
a cardiac stimulation device including shocking charge storage having a capacitance of between 200 and 400 μF and wherein the stimulation device automatically monitors the heart for indications of fibrillation and, upon determining indications of fibrillation, selectively provides a defibrillation stimulation between the first and second electrodes.

5. The appliance of claim 4, wherein the defibrillation stimulation is provided in the range of 100 to 360 volts.

6. The appliance of claim 4, wherein the defibrillation stimulation is provided as a biphasic waveform of less than 15 ms total duration.

7. The appliance of claim 4, wherein the charge storage is configured to store 26 joules or less of energy.

* * * * *

UNITED STATES PATENT AND TRADEMARK OFFICE
CERTIFICATE OF CORRECTION

PATENT NO. : 7,640,065 B1  Page 1 of 1
APPLICATION NO. : 11/378491
DATED : December 29, 2009
INVENTOR(S) : Mark W. Kroll It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 927 days.

Signed and Sealed this

Ninth Day of November, 2010

David J. Kappos
*Director of the United States Patent and Trademark Office*